United States Patent [19]

Benton et al.

[11] Patent Number: 4,876,094
[45] Date of Patent: Oct. 24, 1989

[54] CONTROLLED RELEASE LIQUID DOSAGE FORMULATION

[75] Inventors: Ben F. Benton, Centerburg; David L. Gardner, Bellville, both of Ohio

[73] Assignee: Battelle Development Corporation, Columbus, Ohio

[21] Appl. No.: 884,167

[22] Filed: Jul. 14, 1986

Related U.S. Application Data

[63] Continuation-in-part of Ser. No. 570,469, Jan. 13, 1984, abandoned.

[51] Int. Cl.⁴ ............................................. A61K 47/00
[52] U.S. Cl. ..................................... 424/491; 426/472
[58] Field of Search ..................... 424/491, 460, 469

[56] References Cited

U.S. PATENT DOCUMENTS

| | | | |
|---|---|---|---|
| 2,739,167 | 3/1956 | Conn | 424/491 |
| 2,805,977 | 8/1957 | Robinson et al. | 424/499 |
| 2,937,091 | 5/1960 | Rosenberg | 424/491 |
| 2,973,266 | 2/1961 | Rosenberg | 424/491 |
| 3,109,775 | 11/1963 | Shepard et al. | 424/499 |
| 3,116,206 | 12/1963 | Brynko et al. | 424/491 |
| 3,371,015 | 2/1968 | Sjorgren et al. | 424/499 |
| 4,432,966 | 2/1984 | Zectoun et al. | 424/491 |
| 4,695,467 | 9/1987 | Uemura et al. | 424/489 |

FOREIGN PATENT DOCUMENTS 931149 7/1963 United Kingdom.

Primary Examiner—Thurman K. Page
Assistant Examiner—Leon R. Horne
Attorney, Agent, or Firm—Barry S. Bissell

[57] ABSTRACT

A liquid dual coated dosage formulation sustained release pharmaceutic having substantial shelf life prior to ingestion is disclosed. A dual coating is applied over controlled release cores to form dosage forms and the coatings comprise fats melting at less than approximately 101° F. overcoated with cellulose acetate phthalate or zein. The dual coated dosage forms are dispersed in a sugar based acidic liquid carrier such as high fructose corn syrup and display a shelf life of up to approximately at least 45 days while still retaining their release profiles following ingestion. Cellulose acetate phthalate coated dosage form cores can in addition be dispersed in aqueous liquids of pH <5.

4 Claims, 1 Drawing Sheet

CONTROLLED RELEASE LIQUID DOSAGE FORMULATION

This application is a continuation-in-part of U.S. Ser. No. 570,469 filed Jan. 13, 1984; abandoned.

BACKGROUND OF THE INVENTION

1. Field of the Invention

This invention relates to controlled release pharmaceuticals, specifically dual-coated controlled release dosage form cores as a liquid dosage formulation which have substantial shelf life. More particularly, this invention relates to and discloses liquid suspensions of dual coated dosage forms that retain their controlled release characteristics following ingestion even though dispersed in a liquid medium for a significant period of time prior to use.

2. Description of the Prior Art

Controlled release dosage form cores of medication are well known in the art. Some such medications are prepared as tablets in the form of a therapeutically active core coated with various thicknesses of ingestible materials. Other time release medications take the form of an innocuous core coated with alternating layers of therapeutically active materials and inactive ingestible materials. More recently microcapsules or microspheres, with selected proportions of the microcapsules/microspheres having coatings of differing permeabilities or solubilities, have been placed in conventional gelatin capsules to yield controlled release dosage forms.

Almost all controlled release pharmaceutical dosage form cores to date are solids in the form of tablets, capsules, matrix beads/microspheres microcapsules, and reservoir-type tablets. These dosage form cores are not always advantageous such as for administering time release drugs to very young children or to very old individuals having difficulty swallowing. An easily prepared and versatile liquid controlled release dosage formulation for delivery of a pharmaceutical, especially one which could be prepackaged, would be a significant advancement.

U.S. Pat. No. 2,805,977 (Robinson) discloses a liquid dosage enteric preparation, however, the Robinson formulation does not teach of any formulation having any shelf life prior to administration. Robinson also does not disclose the use of the dual coating of the resent invention so as to yield a liquid suspension of controlled release dosage forms that retains its controlled release characteristics even though dispersed in a liquid medium for a significant period of time prior to use.

DEFINITIONS

"Dosage form" refers to a dual coated core, specifically a core matrix tablet, microcapsule, or matrix bead (also called a microsphere) of less than 1400 microns diameter, comprising a binding material and a contained therapeutically active compound, more particularly is defined as referring to a solid core or housing vehicle containing a therapeutically active compound and exhibiting controlled release characteristics. Over this core, dual coatings are applied. The dual coated core shall be referred to as a dosage form.

"Dosage form cores" refers to cores before application of the dual coatings of the invention.

"Controlled release" is understood to mean release, preferably uniform release, of the active compound over a span of time, thus would encompass such terms as time-release, delayed release, and sustained release.

"Dosage formulation" is defined as referring to the combination of the dual coated dosage form cores and liquid carrier in which the dual coated dosage form cores are dispersed.

A liquid formulation of dual coated dosage form cores following the above definitions, comprises dosage form cores such as matrix beads/microspheres (which can be time release or controlled release devices) containing a therapeutically active compound over which there are applied two unique coatings. These two coatings enable dispersion of the coated dosage form cores in a liquid carrier by imparting stability to the dosage form cores such that no release of therapeutic compounds occurs to an acid liquid carrier over days of exposure; however, a normal release profile of the active therapeutic material is expressed upon changing the dispersion environment of the dual coated dosage form cores to alkaline.

SUMMARY OF THE INVENTION

Figure 1:
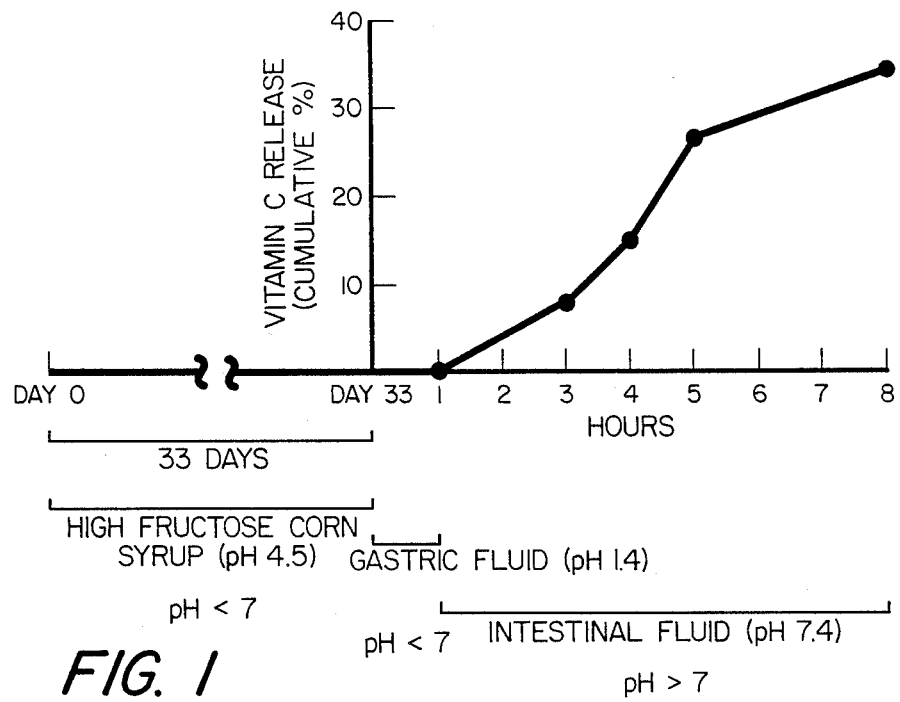
FIG. 1 is a release profile of a Vitamin C dosage form core (microsphere) overcoated with dual coatings according to the invention, namely a fat, 15% by weight, followed by zein, 10% by weight.

It is an object of the present invention to provide a liquid controlled release dosage formulation, especially for pharmaceuticals.

It is an object of this invention to provide a liquid suspension of dual-coated controlled release dosage form cores that retain their controlled release characteristics even though dispersed in a liquid medium for a significant period of time prior to use.

It is a further object of this invention to provide such dual-coated controlled release dosage form cores as an easily prepared and versatile liquid controlled release dosage formulation.

The present invention relates to and discloses compositions for making liquid suspensions of controlled release dosage forms of therapeutically active compounds that retain their controlled release characteristics even though dispersed in a liquid medium for a significant period of time prior to use.

The present invention can be applied to and successfully used with any solid controlled release dosage form core to convert it into a liquid dosage formulation having significant shelf life while still retaining an acceptable controlled release profile upon ingestion.

To achieve what would be considered an easily swallowed liquid formulation, dosage form cores such as microspheres/matrix beads are preferably extremely small such that a suspension is directly formed or upon simple agitation. A formulation akin to a colloidal dispersion is advantageous. A true colloid however is not necessarily formed by the invention since settling of particulate-like dual coated dosage form cores is tolerable as they can be readily agitated to bring about suspension just prior to ingestion. Higher viscosity carrier liquids reduce the rate of settling. Fluids with viscosities similar to corn syrup are preferred.

The present invention discloses use of a unique combination dual coating of fats overcoated with cellulose acetate phthalate or zein and a liquid carrier for achieving a versatile liquid controlled release dosage formulation having substantial shelf life prior to ingestion.

DETAILED DESCRIPTION OF THE INVENTION

The present invention is a controlled release liquid dosage formulation for pharmaceuticals. The present invention discloses use of a unique combination of dual coatings of controlled release type dosage form cores in combination with a liquid carrier. Suitable controlled release type dosage form cores useful in the practice of the present invention include controlled-release matrix beads/microspheres.

The cores used in the invention, matrix bead/microspheres, typically are formed of a binder which is an ingestible material such as a soluble polymer or porous insoluble polymer or a wax such as beeswax which is intimately mixed with the therapeutically active compound.

The ingestible materials useful as the binder are those conventionally employed and include methyl and ethyl cellulose, cellulose acetate and phthalate, shellac, castor oil and hydrogenated castor oil, waxes such as beeswax, carnauba wax, candelilla wax, Japan wax, paraffin, bayberry wax, higher fatty acids, esters of fatty acids such as glyceryl tristearate, cetyl palmitate, diglycol stearate, glyceryl myristate, triethylene glycol monostearate, higher fatty alcohols such as cetyl alcohol and stearyl alcohol, and high molecular weight polyethylene glycols such as the carbowaxes, polyethylene glycol monostearate, polyethylene glycol distearate, polyoxyethylene stearate, glyceryl monostearates and mixtures thereof. The ingestible material is ordinarily intimately admixed with finely divided therapeutically active material while the former is at least partially dissolved in an organic solvent such as methyl alcohol, isopropyl alcohol, carbon tetrachloride, chloroform, or acetone, or thermally liquified. The proportion of therapeutically active compound in relation to binder often is paramountly dictated by the potency of the therapeutically active compound. The binder can comprise as little as 5 or 10% of the core to better than 90% of the core.

Alternative to a homogeneous mixture, a matrix bead/microsphere can be a core mixture of larger fragments of therapeutically active compound together with binder. In another variation, the binder can envelop a fragment of therapeutically active substance forming a microsphere which is essentially a microcapsule. Assorted and various matrix bead and microsphere configurations are in commercial production and are suitable (provided they do not substantially exceed 1400 micron diameter) for dual coating according to the invention to yield a controlled release liquid formulation. It is not a purpose of the invention to disclose a new core.

The invention essentially provides a delivery vehicle and does not appreciably alter the core coated, thus any commercially available core i.e., matrix bead/microsphere would be expected to function in the invention. In fact, in the examples, the invention is illustrated functional with randomly selected cores purchased from different suppliers.

The dosage form cores such as microspheres or matrix beads are coated with two unique materials. The first coating is with a hydrophobic, fat having a melting point of approximately 101° F. or lower such that the coating would be softened and almost liquid or rendered permeable following ingestion. The first coating fat should be ingestible, meaning safe to consume and digestible and have a melting point of less than 101° F. The first coating fat preferably is comprised of glycerides composed of fatty acids of from 3 to 22 carbons, with said glycerides or blends of glycerides having a melting point of 101° F. or less. It is to be understood by those skilled in the art that most fats or glycerides include minor percentages of sterols, hydrocarbons, tocopherols and other nonglyceride constituents. The fats or glycerides can include mono-, di-, or triglycerides. The first coating fat can for example be a hard butter such as theobroma or cocoa butter having a melting point of 86°–95° F., or partially hydrogenated cottonseed and/or soybean vegetable oil such as Kaomel® (Durkee) which has a Wiley melting point of 97°–101° F. Also useful for the first coatings fat are: animal fat, vegetable fat, tallow, shortening, lard, partially hydrogenated vegetable oils, butterfat, or margarine.

It is to be understood that melting point is an approximate term when applied to fats, since these materials melt over a range of temperature. A useful vegetable oil, such as coconut oil, melts at from 21°–25° C. (70°–77° F.).

Melt point determination techniques have been established by the Fat Analysis Committee of the American Oil Chemists' Society such as AOCS Method Cc 2-38 Wiley Melting Point and AOCS Method Cc 3-25 incorporated herein by specific reference.

Over the first coating, an overcoat or second coating is provided which is: (1) amenable to being rendered permeable in early portions of the gastrointestinal tract, preferably within approximately the first hour of entering the gastrointestinal tract; and (2) able to prevent agglomeration or clumping of the coated matrix beads/microspheres.

It is this combination of coatings (first and second overcoating of the microspheres) which permit the dosage form to be successfully placed in a liquid carrier vehicle for at least 45 days prior to ingestion. This combination of dual coatings also helps maintain dispersibility of the dosage forms while physically retaining the therapeutically active compound or active drug within the dosage form prior to actual ingestion of the liquid dosage formulation.

Compounds useful for the second coating or overcoating are zein and cellulose acetate phthalate.

The second coating is nonsoluble in the carrier liquid, but is rendered permeable in the gastrointestinal tract. The second coating is rendered permeable by the action of the slightly acidic or alkaline intestinal fluids, pH>5.5. The above named second coatings are pH sensitive, meaning soluble in only a limited range of pH i.e., essentially alkaline soluble in the GI tract.

Any common plasticizer such as diethyl phthalate, tributyl citrate, tributyrin, triacetin, castor oil, partially or fully acetylated monoglycerides or butyl phthalyl butyl glycolate can also optionally be employed in either or both coatings to impart flexibility to the coating.

The dual coated microspheres, i.e., dual coated controlled release dosage forms of the invention, can then be dispersed in the acidic carrier or delivery liquid medium days in advance of ingestion.

The carrier liquid is an aqueous solution of a sugar and should be viscous meaning having a thickness greater or higher than that of water. The carrier liquid should have a pH<5. If addition of acid such as vinegar is necessary to bring the pH below 5, buffering such as with a phosphate buffer would be appropriate. Most sugars though are naturally acidic.

Sugar refers to nutritive sweeteners and includes the commonly understood sugars of the sweetener industry including honey, cane sugar, beet sugar, maple sugar, and corn sugars or corn syrups. Chemically sugars are saccharides which can, for convenience, be further classed as mono-, di-, oligo, or poly-saccharides. Principal constituents of industrial sugars are sucrose, corn syrup, maltodextrins, glucose, dextrose, fructose, or levulose and lactose. For purposes of this invention, the term reduced sugar includes the reduced sugars such as mannitol, sorbitol or ribitol in which the aldehyde or ketone function is reduced to the alcohol level of oxidation. The sugar syrups optionally can be flavored.

In the preferred embodiment, high fructose corn syrup was found to be a particularly suitable carrier liquid as such syrup has only approximately 30% water and is naturally acidic.

The differences between high fructose corn syrup (HFCS) and other corn syrups is in the pattern of carbohydrate distribution. Corn syrups generally contain no fructose. HFCS, as the name implies, contains this sugar. HFCS is typically 50% dextrose, 42% fructose and other saccharides at 8% on a dry weight basis. To raise the sweetness level, there is a trend in the industry to higher percentages of fructose in the syrup with a consequent reduction in dextrose and other saccharides. Corn syrups and high fructose corn syrups and the industry are further described at length in Pancoast, Harry M.; Junk, W. Ray; *Handbook of Sugars, Second Ed.*, AVI Publishing Co., Westport, Conn., 1980 particularly Chapters 8-10, pages 147-255 incorporated herein by specific reference.

Sugar solutions and sugar syrups as the carrier liquid limit the available water and also act as a preservative.

In the case of cellulose acetate phthalate as the second coating, the carrier aqueous liquid of pH<5 can, in addition, include aqueous liquids other than aqueous solution of sugars. For example, with CAP, aqueous phosphate buffer solutions of pH 4.5 were found to be useful. Such solutions did not work with zein (dumping of therapeutic compound occurred) absent the presence of sugars.

The present invention provides an improved delivery vehicle for controlled release dosage form, cores i.e., dual coated matrix beads/microspheres, by enabling preparing of liquid formulations of such dosage forms having a substantial shelf life. Dual coated microspheres/matrix beads are preferred dosage forms, especially in the size range of 15-300 microns. Sizes up to 1600 microns (1400 micron cores before dual coating) can also be used if settling can be tolerated. With applications for young children, more viscous carrier liquids would be preferred to minimize settling of dosage forms providing uniformity of dosages.

Controlled release dosage form cores (microspheres/matrix beads) useful for the purposes of being dual coated according to the invention, can be prepared by any of several known microencapsulation processes including pan coating, prilling, granulation fluidization processes, pressing through fine mesh screens and other processes.

Commercially available microspheres or matrix beads can be used.

Dosage form cores of matrix beads/microspheres are illustrated by such U.S. patents as Raghunathan U.S. Pat. Nos. 4,221,778; Berger 3,344,029; Ogawa et.al. 4,261,970; and Bardani 2,928,770.

The advantage of the present invention is that it enables the dosage forms to be formulated as a stable liquid dispersion not releasing therapeutic compound for days. Only after ingestion is the original release profile of the dosage form core expressed.

The cores such as matrix beads/microspheres can be coated by any of the coating techniques known in the art including fluidized bed processes (see for example U.S. Pat. No. 4,117,801), emulsion techniques, spray coating, dipping or rolling.

Each coating of the two coatings applied to the matrix bead/microsphere should be not more than 100 microns in thickness.

The preferred dual coatings comprise a first coating of fat at 4.8 to 17.7% by weight (100 microns or less in thickness) followed by a coating of zein or cellulose acetate phthalate at 2.3 to 10% by weight (also 100 microns or less in thickness). The percentages by weight are based on the weight of the total dual coated dosage form core.

This invention is particularly suitable for controlled release microspheres packageable and administrable in a liquid formulation intended for young children or the elderly.

The liquid suspension of dual coated controlled release dosage form cores according to this invention can be prepared in advance as a liquid formulation in many cases as early as 45 days or sooner before the intended day of administration of the liquid formulation. Upon ingestion of the liquid dosage formulation, the controlled release characteristics of the dual coated dosage form cores are expressed with active drug release commencing in the upper gastrointestinal tract and active drug release continuing at a uniform rate thereafter for at least 8-12 or to 24 hours.

The controlled release liquid dosage formulations of the present invention are particularly suitable for dosage form cores (microspheres) containing theophylline or Vitamin C. It is expected the invention will work equally as well for dimethylxanthine, antihistamines, cold formulations, analgesics, amino acid supplements, vitamins, geriatric drugs such as sleeping aids and blood pressure regulators, antidepressants such as lithium chloride, also potassium salts, and alkaloids such as caffeine and codeine.

The following examples serve to illustrate the invention, however, the invention is not to be construed as limited thereto.

EXAMPLE 1

Theophylline was selected as the drug to illustrate the dual coated dosage form core and liquid dosage formulation of the present invention. Theophylline was selected to illustrate the scope of the invention since a suitable liquid dosage formulation, especially one in which theophylline is the therapeutically active compound, must satisfy a particularly rigid controlled-release profile.

Theophylline is a representative alkaloid drug. It is isomeric with dimethylxanthine and the common alkaloid, caffeine, differs from theophylline by one less methyl group. Theophylline, typical of alkaloids, is bitter.

Theophylline is used as an antiasthmatic but it has an unpleasant taste and requires careful dose measurement and administration to maintain therapeutic serum concentrations. Especially with young children, the now required every 4–6 hour round-the-clock dosing levels of theophylline are difficult to administer and maintain. Children often dislike the taste.

It is held by some in the field that theophylline is a tissue irritant and thus is preferred to be administered in an enteric release form.

Thus, the preferred controlled release liquid dosage formulation containing theophylline according to this invention should satisfy the rigid criteria of:

1. withhold release of the active compound to the carrier liquid when stored as a liquid formulation so as to have significant shelf life, preferably at least 35 days;

2. begin release of the active compound approximately one hour after entering the gastrointestinal tract;

3. continue uniform sustained release of the active drug for at least 8 to 24 hours.

The liquid dosage formulation of the present invention would be particularly advantageous for the administration of theophylline. A liquid dosage formulation sustaining theophylline release up to 12 or 24 hours according to this invention would be particularly beneficial to asthmatic children, would be easy to administer because of the liquid carrier and its masking of the unpleasant taste, and would require less frequent administration.

With a stable shelf life in excess of 35 days, the premixed liquid dosage formulation would be practical for dispensing by pharmacies.

Examples of five commercially available controlled release type dosage form cores are illustrated below. The active drug is theophylline.

1. Aerolate®, 1, 2 and 4 grain capsules (Flemming and Company, St. Louis, Mo.).

2. Theo-Dur®, 100, 200 and 300 mg scored tablets (Key Pharmaceuticals, Inc., Miami Fla.).

3. Theo-Dur Sprinkle® milligram strength microspheres, 50, 75, 125 and 200 mg strengths (Key Pharmaceuticals, Inc., Miami, Fla.).

4. Slo-Phylline Gyrocaps®, 60, 125 and 250 mg capsules (Dooner Laboratories, Inc., Haverhill, Mass.).

5. Sustaire® tablet (Roerig, Division of Pfizer, Inc., New York, N.Y.).

Based upon the release profile of these sustained release type products, the Theo-Dur® scored tablets and Slo-Phylline Gyrocaps® when placed into applesauce exemplify the typical "liquid dosage formulation" available today. Tested for release of theophylline via serum levels it was found that after one hour, the Theo-Dur® scored tablets had released 10% of their theophylline and the Slo-Phylline Gyrocaps® had released 80% of their theophylline. The typical controlled release dosage form available today does not have any significant shelf life in an aqueous based carrier fluid since appreciable release proceeds from the initial time of dispersion in the carrier liquid.

SOURCE OF TYPICAL CONTROLLED RELEASE TEST

Typical sustained release in the form of spherical beads or microspheres are readily obtained from commercial sources In this case, matrix beads/microspheres employing a wax matrix (600–800 micron diameter) were obtained from Central Pharmaceuticals, Inc., 110-128 E. Third Street, Seymour, Ind. The following analysis was provided:

TABLE 1

Product 48.15% theophylline anhydrous sustained release beads

| Analyzed For | Label Claim | Found | % of Claim |
|---|---|---|---|
| Theophylline Anhydrous | 48.15% | 49.4% | 102.6% |

Release Rate: Method - USP dissolution apparatus 2 operated at 50 RPM
Released in:

| | | Limits |
|---|---|---|
| 1 hour | 10.1% | 5.0–20.0% |
| 2 hours | 27.9% | 20.0–40.0% |
| 4 hours | 61.0% | 50.0–85.0% |
| 6 hours | 79.3% | NLT 65.0% |
| 8 hours | 89.1% | NLT 85.0% |

PROCESS FOR COATING CONTROLLED RELEASE TEST DOSAGE FORMS

In a fluidized bed process the above mentioned controlled release test dosage form cores in the form of spherical matrix beads/microspheres containing theophylline were sprayed with a solvent solution of Kaomel® (Durkee) which is a partially hydrogenated cottonseed and soybean vegetable oil. This oil has a Wiley melting point of 97°–101° F. and solid fat index (SFI) values as follows: 50° F.=69% min; 70° F.=54% min; 80° F.=53% min; 92° F.=22% min; 100° F.=5% max.

The Kaomel® coated beads were then further coated either with zein or cellulose acetate phthalate (CAP). A plasticizer was included to enhance the coating properties of the zein and CAP. With zein, the plasticizer used was Myvacet® (Eastman Kodak) a distilled acetylated monoglyceride. With cellulose acetate phthalate, a butyl phthalyl-butyl glycolate liquid sold as Sanitizer® (Pfizer) was used as a plasticizer.

The following types of single and dual coated dosage forms were prepared for testing (all percents given are by weight).

TABLE 2

1 - uncoated dosage form core (matrix bead/microsphere from Central Pharmaceuticals, Inc.)
2 - dosage form core coated with 17.7% Kaomel®
3 - dosage form core coated with 17.7% Kaomel® followed by 4.33% cellulose acetate phthalate
4 - dosage form core coated with 17.7% Kaomel® followed by 4.33% cellulose acetate phthalate containing 1.7% plasticizer
5 - dosage form core coated with 17.7% Kaomel followed by 4.0% zein containing 0.9% plasticizer
6 - dosage form core coated with 17.7% Kaomel® followed by 2.2% zein containing 0.9% plasticizer
7 - dosage form core coated with 4.76% Kaomel® followed by 2.37% cellulose acetate phthalate containing 1.0% plasticizer
8 - dosage form core coated with 4.78% cellulose acetate phthalate containing 1.92% plasticizer
9 - dosage form core coated with 2.41% cellulose acetate phthalate containing 0.97% plasticizer
10 - dosage form core coated with 4.76% Kaomel®

All percentages are on the basis of total weight of coated dosage form

Four release tests (A thru D below) were designed to assess release characteristics of the various coated and uncoated dosage form cores.

ASSESSMENT OF RELEASE TO LIQUID CARRIER (A) dosage form placed in a high fructose corn syrup solution and theophylline release determined after 7 or 14 days.

(B) dosage form placed in a phosphate buffer (pH 6.0) and release of theophylline determined after 1, 3 and 7 days.

(C) dosage form placed in a phosphate buffer (pH ~4.5) and release of theophylline determined after 1, 3 and 7 days.

ASSESSMENT OF RELEASE PROFILE IN GASTROINTESTINAL TRACT (D) dosage form placed in simulated gastric fluid (pH 1.2) for one hour, followed by placement in simulated intestinal fluid (pH 7.5) over the next 7 hours. Theophylline release was determined at 1, 2, 3, 4, 5, 6 and 8 hours.

In conducting the (B) and (C) in vitro release studies, approximately 100 milligrams of selected dosage forms were placed in a test tube containing 10 ml of the phosphate buffer (either pH 6.0 or pH 4.5) test solution. These studies were conducted at ambient temperature with the test tube contents mixed via a Lab Quake test tube rotator. At predetermined times, the test solution was drawn off. Fresh test solution was then added back to the test tube. The procedure of drawing off the test solution was performed on days 1, 3 and 7. The test solutions removed on days 1, 3 and 7 were filtered and refrigerated until assayed for theophylline.

In conducting the (A) in vitro release study, the principal difference was that high fructose corn syrup (HFCS, Corn Sweet® 42, Archer Daniels Midland Co.) was substituted as the test solution for the phosphate buffer. Other aspects of this in vitro release study were similar to those described for (B) and (C).

The (D) in vitro release study was similar to the (B) and (C) in vitro release studies with the exception of duration, temperature and test solution. All (D) in vitro release studies were conducted at 37 C by placing the test tubes on the Lab Quake rotator in a thermostatistically-controlled oven. The test solution for this in vitro release study was a simulated gastric fluid during the first hour followed by a simulated intestinal fluid.

The simulated gastric fluid was prepared as follows:

2.0 g of sodium chloride and 3.2 g of pepsin was dissolved in 7.0 ml of hydrochloric acid and sufficient water to make a 1000 ml solution. This test solution has a pH of about 1.2.

The simulated intestinal fluid was prepared as follows:

6.8 g of monobasic potassium phosphate was dissolved in 250 ml of water. With stirring, 190 ml of 0.2 N sodium hydroxide was added along with 400 ml of water. 10 g of pancreatin was then added with stirring. The pH of the resulting solution was adjusted to a pH of 7.5±0.1 by the addition of 0.2N sodium hydroxide, then the solution was diluted with water to 1000 ml.

Theophylline release in the simulated gastric fluid test solution, followed by simulated intestinal fluid test solution, was determined at the end of 1, 2, 3, 4, 5, 6 and 8 hours.

In all the in vitro release studies, A through D, theophylline was assayed by a reverse phase high pressure liquid chromatography (HPLC) technique as set forth by L.C. Franconi et. al., "Determination of Theophylline in Plasma Ultrafiltrate by Reversed Phase High Pressure Liquid Chromatography", Anal Chem., 48: 372, 1976.

The results of the (A) in vitro release study (Table 3) show that when the dosage form is placed in high fructose corn syrup, HFCS, an acidic environment, several dosage forms show extremely low levels of theophylline release In particular, type #4 dosage form released only 0.2 percent of the available theophylline over a 14-day period. The uncoated dosage form under these same conditions and duration released 14.8% of the available theophylline. Another four types #'s 5, 7, 8 and 10 exhibited less than 1 percent release after 7 days. The reduced amount of theophylline released is due primarily to the coatings placed over the controlled release dosage forms. The low percentage of water in the HFCS, i.e., 29 percent, tends to further minimize the amount of theophylline which is released. Theophylline solubility in water=8.3 mg/ml. The results of the (B) and (C) in vitro release studies (Tables 4 and 5) verify the importance of the liquid carrier pH in which the dosage form will be eventually formulated. For instance, in Table 4, the lowest percentage of theophylline release from the #4 type dosage form was 47.1%. However, in Table 5, when this same type #4 dosage form was placed in an acidic environment (pH 4.5), the theophylline release had dropped to 1.8%. Additionally, the dosage form overcoated with Kaomel®-CAP produced the least amount of theophylline release. The importance of these two coatings, i.e., Kaomel® and CAP, is clearly established if compared with dosage form types #8 and #9 (See Table 5).

TABLE 3

Results of In Vitro Release Study (A)
High Fructose Corn Syrup Solution (HFCS)

| Coating* | Prill Type (see Table 2) | Weight, mg | Available Theophylline, mg | Day (mg Theophylline Released) 7th day | 14th day | Total Theophylline Released, mg | % of Available Theophylline Released |
|---|---|---|---|---|---|---|---|
| u | #1 | 102.3 | 50.5 | 6.85 | | 6.85 | 13.6 |
| k/c | #4 | 105.5 | 39.8 | 0.04 | 0.04 | 0.08 | 0.2 |
| u | #1 | 102.5 | 50.6 | 2.89 | 4.58 | 7.47 | 14.8 |
| u | #1 | 499.4 | 240.5 | 15.21 | | 15.21 | 6.2 |
| k | #10 | 525.0 | 240.2 | 1.84 | | 1.84 | 0.7 |
| c | #8 | 535.5 | 239.8 | 0.30 | | 0.30 | 0.1 |
| k/z | #5 | 630.4 | 224.6 | 1.63 | | 1.63 | 0.7 |

TABLE 3-continued

Results of In Vitro Release Study (A)
High Fructose Corn Syrup Solution (HFCS)

| Coating* | Prill Type (see Table 2) | Weight, mg | Available Theophylline, mg | Day (mg Theophylline Released) 7th day | Day (mg Theophylline Released) 14th day | Total Theophylline Released, mg | % of Available Theophylline Released |
|---|---|---|---|---|---|---|---|
| k/c | #7 | 540.2 | 238.0 | 1.04 | | 1.04 | 0.4 |

*u = uncoated
k = Kaomel ®
c = cellulose acetate pthalate
k/c = Kaomel ® overcoated with cellulose acetate pthalate
z = zein
k/z = Kaomel ® overcoated with zein

TABLE 4

Results of In Vitro Release Study (B)
pH 6.0 Studies

| Coating | Type of Prill (Refer to Table 2) | Weight, mg | Day (mg Theophylline Released) 1 | 3 | 7 | Total Theophylline Released, mg | % of Available Theophylline Released |
|---|---|---|---|---|---|---|---|
| u | #1 | 102.5 | 27.8 | 12.6 | 0.7 | 41.1 | 81.1 |
| u | #1 | 102.2 | 20.6 | 5.9 | 0.3 | 26.7 | 52.9 |
| u | #1 | 103.8 | 26.9 | 8.0 | 0.6 | 35.5 | 69.1 |
| k | #2 | 103.5 | 0.7 | 4.5 | 11.6 | 16.8 | 39.8 |
| k | #2 | 103.7 | 1.6 | 3.6 | 8.9 | 14.1 | 33.4 |
| k/c | #3* | 102.9 | 19.0 | 1.9 | 0.0 | 20.9 | 41.1 |
| k/c | #3 | 103.9 | 4.7 | 6.9 | 25.2 | 36.7 | 91.8 |
| k/c | #4* | 103.3 | 18.4 | 6.9 | 0.5 | 25.8 | 61.3 |
| k/c | #4 | 103.3 | 0.3 | 3.4 | 14.6 | 18.3 | 47.1 |
| k/z | #5 | 106.6 | 0.1 | 0.6 | 10.3 | 11.0 | 26.6 |
| k/c | #7 | 106.1 | 10.7 | 24.8 | 4.0 | 39.6 | 82.2 |
| c | #8 | 105.2 | 26.8 | 9.9 | 0.5 | 37.2 | 76.6 |
| c | #9 | 106.1 | 25.5 | 9.8 | 0.8 | 36.0 | 71.2 |

*10 ml liters of Triton ® x-100 surfactant added to test solution. (Because of high levels of release on day 1, addition of surfactant to the carrier liquid is contra-indicated and therefore not prefered in this invention.)

TABLE 5

Results of In Vitro Release Study (C)
pH 4.5 Studies

| Coating | Type of Prill (Refer to Table 2) | Weight, mg | Day (mg Theophylline Released) 1 | 3 | 7 | Total Theophylline Released, mg | % of Available Theophylline Released |
|---|---|---|---|---|---|---|---|
| k/c | #3 | 104.9 | 3.4 | 7.8 | 19.4 | 30.7 | 75.8 |
| k/c | #4 | 105.1 | 0.1 | 0.2 | 0.5 | 0.8 | 1.8 |
| k/z | #5 | 104.8 | 0.1 | 0.8 | 9.3 | 10.2 | 25.0 |
| k/z | #6 | 105.4 | 0.1 | 0.2 | 1.0 | 1.3 | 3.1 |
| k/c | #7 | 105.1 | 1.0 | 10.5 | 16.8 | 28.3 | 59.2 |
| c | #8 | 107.9 | 1.1 | 3.5 | 5.8 | 10.4 | 21.4 |
| c | #9 | 105.5 | 1.1 | 5.5 | 13.6 | 20.2 | 40.2 |

3 - prills did not possess good morphology
7 - both the Kaomel ®, CAP and plasticizer level were reduced as compared to #4

Since only a very small percentage of theophylline release had occurred over a 7 day period with the type #4 dosage form in an acidic environment, this same type dosage form was followed for 35 days in a pH4.5 phosphate buffer solution In this study, the total theophylline released over a 35 day period was determined to be 5.85% (See Table 6). This figure is believed to be upwardly biased since the test solution was changed every 7 days with fresh test solution. This changing of solution increased the concentration gradient between the coated dosage forms and the liquid environment Absent the solution changing, the actual amount of theophylline released would approximate 1.3%. This is based upon the fact that the actual amount of theophylline released at the end of each 7 day period approximated 0.4–0.5 mg. The total amount of theophylline originally available for release from the type #4 prill was 39.3 milligrams, i.e., 0.5÷39.3=1.3 percent.

This latter study represents a situation in which the medium is essentially 100% water. Thus, even under these severe test conditions, very little theophylline was released. Thus, the importance of these coatings, as they relate to the pH of the liquid environment, is demonstrated.

It can be seen from Table 7 that the dosage form overcoated with cellulose acetate phthalate alone does not yield an acceptable controlled release characteristic as such dosage forms release a high burst of theophylline release in the second hour of the test. The release rates of the CAP alone coated dosage forms was similar to that of the uncoated dosage forms. Kaomel ® alone as a coating was found to be unworkable, primarily because of problems of clumping or aggregation. This clumping or aggregation was due to softening of the fat in the in vitro release studies conducted at 37° C.

TABLE 6
Release of Theophylline From Dosage Form Over a 35-Day Period
(pH 4.5 phosphate buffer solution)

| Coating | Type of Dosage Form (Refer to Table 2) | Weight | 7 | 14 | 21 | 28 | 35 | Total Theophylline Released, mg | % |
|---|---|---|---|---|---|---|---|---|---|
| k/c | #4 | 104.2 | 0.4 | 0.4 | 0.5 | 0.5 | 0.5 | 2.3 | 5.9 |

TABLE 7
Results of In Vitro (D) Release Study
(Synthetic Gastric Then Synthetic Intestinal Solution)

| Coating | Dosage Form Type (see Table 2) | Weight, mg | 1 | 2 | 3 | 4 | 5 | 6 | 8 | Total Theophylline Released, mg | % of Available Theophylline Released |
|---|---|---|---|---|---|---|---|---|---|---|---|
| u | #1 | 101.0 | 9.6 | 5.1 | 4.7 | 4.0 | 4.0 | 3.2 | 3.4 | 34.1 | 68.3 |
| (17.7%) k | #2 | 102.9 | 0.1 | 0.2 | 0.8 | 0.9 | 1.2 | 2.1 | 4.3 | 9.5 | 22.8 |
| k/c | #3 | 104.8 | 0.1 | 0.7 | 1.3 | 1.4 | 1.6 | 2.2 | 5.5 | 12.9 | 31.9 |
| k/c | #4 | 106.3 | 0.0 | 0.1 | 0.5 | 0.8 | 1.0 | 1.5 | 3.3 | 7.3 | 18.1 |
| k/z | #5 | 105.5 | 0.1 | 0.7 | 4.7 | 12.9 | 8.5 | 3.1 | 0.2 | 30.3 | 74.1 |
| k/z | #6 | 106.3 | 0.0 | 0.3 | 1.5 | 2.2 | 7.1 | 8.0 | 9.5 | 28.7 | 68.9 |
| (4.8%) k | #10 | 105.4 | 0.4 | 3.2 | 5.0 | 6.3 | 8.2 | 7.2 | 12.3 | 42.7 | 86.0 |
| k/c | #7 | 106.2 | 0.1 | 1.8 | 3.1 | 4.5 | 5.7 | 7.3 | 18.5 | 41.1 | 85.2 |
| c | #8 | 107.0 | 0.2 | 23.8 | 6.1 | 0.2 | 0.0 | 0.0 | 0.0 | 30.4 | 61.6 |
| c | #9 | 107.0 | 0.3 | 34.3 | 4.8 | 0.3 | 0.0 | 0.0 | 0.0 | 39.8 | 77.8 |

Various coating levels of fat (Kaomel®) alone produced dumping in the in vitro release studies, tending to reduce the available surface area and thus giving rise to questions as to reproducibility of the theophylline release profile. The present invention unexpectedly requires a dual coated dosage form to provide a liquid suspension (dosage formulations) having substantial shelf life that retains its controlled release characteristics.

Table 8 illustrates that the dosage forms which were followed (4, 5, 7, & 8) in three different liquid carriers (high fructose corn syrup, phosphate buffer pH 4.5, and phosphate buffer pH 6.0) showed differences in release depending on the type of liquid carrier and dosage form. Especially with zein as the outer coating, the carrier liquid must be a sugar solution such as high fructose corn syrup. This carrier liquid is also preferred with cellulose acetate phthalate. The precise reason why sugar based carrier liquids restrict release from zein coated dosage form cores differently than other aqueous fluids is not precisely understood though in part it may be related to the amount of available water in such carrier liquids.

EXAMPLE 2.

A sustained-release Vitamin C product (dosage form core) was overcoated with the dual coatings, namely a fat (Kaomel) and zein, a fat and cellulose acetate phthalate, cocoa butter and zein, also cocoa butter and cellulose acetate phthalate.

Vitamin C was selected since it is 40× more soluble in water than theophylline.

Solubility in water: Theophylline - 8.3 mg/ml; Vitamin C - 333 mg/ml.

TABLE 8

| Phosphate Buffers | | |
|---|---|---|
| pH 4.5 | pH 6.0 | HFCS |

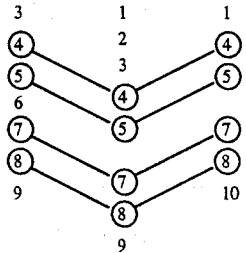

| COMPOSITION (Percentages by Weight) | | | | |
|---|---|---|---|---|
| Dosage Form | % Kaomel ® | % CAP | % Zein | % Plasticizer |
| 4 | 17.7 | 4.33 | | 1.7 |
| 5 | 17.7 | | 4.0 | 0.9 |
| 7 | 4.8 | 2.37 | | 1.0 |
| 8 | | 4.78 | | 1.9 |

| RELEASE TO CARRIER LIQUID HFCS (pH 4.5) | | | | |
|---|---|---|---|---|
| Dosage Form | 7 Days | 14 Days | Total | Percent |
| 4 | 0.04 | 0.04 | 0.08 | 0.2 |
| 5 | 1.63 | | 1.63 | 0.7 |
| 7 | 1.04 | | 1.04 | 0.4 |
| 8 | 0.30 | | 0.30 | 0.1 |

| Phosphate Buffer (pH 4.5) | | | | |
|---|---|---|---|---|
| Dosage Form | 1 Day | 3 Days | 7 Days | Total | Percent |
| 4 | 0.1 | 0.2 | 0.5 | 0.8 | 1.8 |
| 5 | 0.1 | 0.8 | 9.3 | 10.2 | 25.0 |
| 7 | 1.0 | 10.5 | 16.8 | 28.3 | 59.2 |
| 8 | 1.1 | 3.5 | 5.8 | 10.4 | 21.4 |

| Phosphate Buffer (pH 6.0) | | | | |
|---|---|---|---|---|
| Dosage Form | 1 Day | 3 Days | 7 Days | Total | Percent |
| 4 | 0.3 | 3.4 | 14.6 | 18.3 | 47.1 |
| 5 | 0.1 | 0.6 | 10.3 | 11.0 | 26.6 |
| 7 | 10.7 | 24.8 | 4.0 | 39.6 | 82.2 |
| 8 | 26.8 | 9.9 | 0.5 | 37.2 | 76.6 |

Vitamin C matrix beads/microspheres were obtained by opening a commercial Vitamin C gelatin capsule (500 mg Vitamin C) containing the matrix beads/microspheres (dosage form core).

The Vitamin C dosage form core was approximately 80 percent Vitamin C and 20 percent binder. The Vitamin C matrix beads/microspheres were 1190-1400 μm diameter.

In a fluidized bed process the Vitamin C matrix beads/microspheres were spray coated as follows: (The percentages given are percent by weight based on the weight of the total coated matrix bead/microsphere.)

Formulation B 15% Kaomel followed by 10% zein

Formulation C 15% Kaomel followed by 10% cellulose acetate phthalate

Formulation D 7.5% cocoa butter followed by 10% zein

Formulation E 7.5% cocoa butter followed by 10% cellulose acetate phthalate.

The above dual coated formulations over the sustained release Vitamin C matrix beads/microspheres prevented release of the Vitamin C to a high fructose corn syrup carrier liquid over a 45 day period. The test tubes were placed in a test tube rotator housed in a dark environment.

For each of the above storage stability tests, 100 mg of the overcoated Vitamin C matrix beads/microspheres were placed in 10 milliliters of high fructose corn syrup.

Uncoated Vitamin C matrix beads/microspheres were used as a control.

TABLE 9
FORMULATIONS USED TO OVERCOAT SUSTAINED RELEASE VITAMIN C PRODUCT (DOSAGE FORM)

| Ingredients | B | C | D | E |
|---|---|---|---|---|
| Vitamin C beads | 1100 g | 1100 g | 1100 g | 1100 g |
| Kaomel | 165 g | 165 g | | |
| Cocoa Butter | | | 82.5 g | 82.5 g |
| Zein | 110 g | | 110 g | |
| Cellulose acetate phthalate | | 110 g | | 110 g |
| Myvacet 9-40 | 16.5 g | | 16.5 g | |
| Myvacet 5-07 | 5.5 g | | 5.5 g | |
| Sanitizer B-16 | | 44 g | | 14 g |

Formulation B yields a Vitamin C Product overcoated with 15 percent Kaomel and 10 percent zein.
Formulation C yields a Vitamin C product overcoated with 15 percent Kaomel and 10 percent cellulose acetate phthalate.
Formulation D yields a Vitamin C product overcoated with 7.5 percent cocoa butter and 10 percent zein.
Formulation E yields a Vitamnn C product overcoated with 7.5 percent cocoa butter and 10 percent cellulose acetate phthalate.

TABLE 10
RELEASE OF VITAMIN C INTO TEST SOLUTION (29-Day Assay)

| Product | Test Solution, 10 ml | mgs Vitamin C Released |
|---|---|---|
| A* | HFCS | 24.0 |
| B | HFCS | 0 |
| C | HFCS | 0 |
| D | HFCS | 0 |
| E | HFCS | 0 |

*Formulation A is an uncoated dosage form core control

TABLE 11
RELEASE OF VITAMIN C INTO TEST SOLUTION (45-Day Assay)

| Product | Test Solution, 10 ml | mgs Vitamin C Released |
|---|---|---|
| A* | HFCS | 22.2 |
| B | HFCS | 0.1 |
| C | HFCS | 0.1 |
| D | HFCS | 0.05 |
| E | HFCS | 0 |

*Formulation A is an uncoated control

The uncoated Vitamin C matrix bead/microspheres (referred to as A) in the carrier fluid released substantial quantities of the therapeutically active compound to the carrier liquid.

In contrast, the dual coated Vitamin C matrix bead/microspheres in the carrier fluid for 29 days exhibited no detectable release and after 45 days, little perceptible release occurred.

Figure 2:
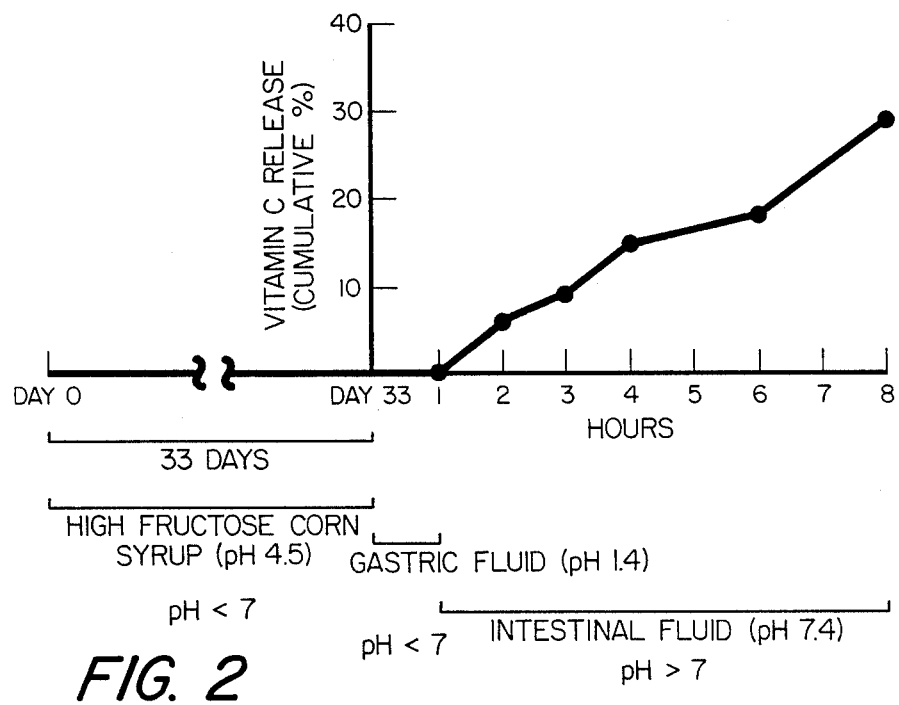
FIG. 2 is a release profile of a Vitamin C dosage form core (microsphere) overcoated with dual coatings according to the invention, namely cocoa butter, 7.5% by weight, followed by cellulose acetate phthalate, 10% by weight.

A sampling of the dosage form (coated microspheres) dispersed in the acidic carrier fluid; i.e., liquid formulation, were examined for their in vitro release profile after 33 days by placement in gastric fluid for 1 hour followed by placement in intestinal fluid. The release profile for formulation B is graphed in FIG. 1. The release profile for formulation E is graphed in FIG. 2. Upon exposure to the intestinal fluid, the release profile graphs clearly demonstrate that a sustained release profile (relatively linear) and approaching zero order was expressed.

The principals, preferred embodiments, and modes of operation of the present invention, have been described in the foregoing specification. The invention which is intended to be protected herein, however, is not to be construed as limited to the particular forms disclosed, since these are to be regarded as illustrative rather than restrictive. Variations and changes can be made by those skilled in the art without departing from the spirit and scope of the invention.

We claim:

1. A drinkable liquid suspension of solid dosage forms consisting of dual coated theophylline cores in an acidic carrier liquid comprising:
    cores of not more than 1400 microns in diameter consisting of a solid binding material and a therapeutically active substance,
    dual coatings consisting of a first coating and a second coating over said cores for retarding release of the therapeutically active substance to the acidic carrier liquid and for permitting release in an alkaline environment,
    the first coating comprising an ingestible fat having a melting point of 101° F. or less, the first coating comprising 4.8 to 17.7% by weight of the total weight of the dosage forms,
    the second coating comprising zein, the second coating comprising 2.3 to 10% by weight of the total weight of the dosage forms,
    a carrier liquid for suspending the dosage forms, the carrier liquid having a pH<5 and comprising a viscous aqueous solution of a sugar.

2. The liquid suspension of solid dosage forms according to claim 1 wherein the first coating is selected from the group consisting of butter, margarine, cocoa butter, vegetable oil or vegetable fat.

3. The liquid suspension of solid particulate-like dosage forms according to claim 1 wherein the carrier liquid is corn syrup.

4. The liquid suspension of solid dosage forms according to claim 3 wherein the corn syrup is high fructose corn syrup.

* * * * *